US007945308B2

(12) United States Patent
Tropp et al.

(10) Patent No.: US 7,945,308 B2
(45) Date of Patent: May 17, 2011

(54) SYSTEMS, METHODS AND APPARATUS FOR AN ENDO-RECTAL RECEIVE-ONLY PROBE

(75) Inventors: James S. Tropp, Berkeley, CA (US); Paul D. Calderon, Castro Valley, CA (US); Daniel Blackburn Vigneron, Corte Madera, CA (US); Lucas Guillermo Carvajal, San Francisco, CA (US); Konstantinos George Karpodinis, Redding, CA (US)

(73) Assignee: General Electric Company, Schenectady, NY (US)

( * ) Notice: Subject to any disclaimer, the term of this patent is extended or adjusted under 35 U.S.C. 154(b) by 387 days.

(21) Appl. No.: 11/320,361

(22) Filed: Dec. 27, 2005

(65) Prior Publication Data
US 2007/0167725 A1   Jul. 19, 2007

(51) Int. Cl.
*A61B 5/05* (2006.01)
(52) U.S. Cl. .................................. 600/423; 600/420
(58) Field of Classification Search .................. 600/407, 600/410–411, 421–423; 324/309, 318–319, 324/322; 128/653.2–653.3
See application file for complete search history.

(56) References Cited

U.S. PATENT DOCUMENTS

| | | | | |
|---|---|---|---|---|
| 4,620,155 A * | 10/1986 | Edelstein | ........................ | 324/322 |
| 4,742,304 A * | 5/1988 | Schnall et al. | ................. | 324/318 |
| 4,792,759 A * | 12/1988 | Keren et al. | .................... | 324/322 |
| 5,041,790 A * | 8/1991 | Tropp et al. | .................... | 324/318 |
| 5,050,607 A * | 9/1991 | Bradley et al. | ................. | 600/423 |
| 5,168,230 A * | 12/1992 | Hashoian et al. | ............. | 324/318 |
| 5,243,289 A * | 9/1993 | Blum et al. | ..................... | 324/322 |
| 5,476,095 A * | 12/1995 | Schnall et al. | ................. | 600/423 |
| 5,669,801 A * | 9/1997 | Lee | .................................. | 445/24 |
| 5,680,047 A * | 10/1997 | Srinivasan et al. | ............ | 324/318 |
| 5,999,000 A * | 12/1999 | Srinivasan | ..................... | 324/318 |
| 6,051,974 A * | 4/2000 | Reisker et al. | ................. | 324/318 |
| 6,081,120 A * | 6/2000 | Shen | .............................. | 324/318 |
| 6,201,392 B1 * | 3/2001 | Anderson et al. | ............. | 324/300 |
| 6,263,229 B1 * | 7/2001 | Atalar et al. | ................... | 600/423 |
| 6,400,154 B2 * | 6/2002 | Tomanek et al. | ............. | 324/318 |
| 6,437,569 B1 * | 8/2002 | Minkoff et al. | ................ | 324/318 |
| 6,501,980 B1 * | 12/2002 | Carlon et al. | ................... | 600/423 |
| 6,628,980 B2 * | 9/2003 | Atalar et al. | ................... | 600/423 |
| 6,747,454 B2 * | 6/2004 | Belt | ................................ | 324/318 |
| 6,831,460 B2 * | 12/2004 | Reisker et al. | ................. | 324/318 |
| 6,898,454 B2 * | 5/2005 | Atalar et al. | ................... | 600/410 |
| 7,084,629 B2 * | 8/2006 | Monski et al. | ................ | 324/318 |
| 7,119,541 B2 * | 10/2006 | Barberi | ......................... | 324/318 |
| 7,160,258 B2 * | 1/2007 | Imran et al. | .................... | 600/593 |
| 2002/0198470 A1 * | 12/2002 | Imran et al. | .................... | 600/587 |

(Continued)

OTHER PUBLICATIONS

Lombardi J. et al, "The use of 13C-magnetic resonance spectroscopy in metabolic research", Nutritional Biochemistry 651 6-521, 1995.

(Continued)

*Primary Examiner* — Francis Jaworski
(74) *Attorney, Agent, or Firm* — Jean Tibbetts, Esq.; Michael G. Smith, Esq.; Ellis B. Ramirez, Esq.

(57) ABSTRACT

Systems, methods and apparatus are provided through which a compact pod insertable into the rectum for Magnetic Resonance Imaging/Magnetic Resonance Spectroscopy (MRI/MRS) examination of the prostate and containing two receive coils, each connected to transmit blocking and pre-tuned trap circuitry which can be superimposed within the pod in close proximity, can, without either circuit interfering with the other, efficiently gather, for imaging and tissue analysis, radio frequency signals emanating from magnetically disturbed nuclei in prostate tissue.

21 Claims, 7 Drawing Sheets

U.S. PATENT DOCUMENTS

2004/0068204 A1* 4/2004 Imran et al. .................. 600/593
2004/0162501 A1* 8/2004 Imran ........................... 600/547

OTHER PUBLICATIONS

MD Schnall, Y Mai, J Tomaszewski, HM Pollack, RE Lenkinski and HY Kressel, "Prostate Cancer: Local Staging with endorectal Surface Coil MR Imaging" Radiology, vol. 178, 797-802, 1991.

Noworolski SM, Henry RG, Vigneron DB, Kurhanewicz J., "Dynamic Contrast-Enhanced MRI in Normal and Abnormal Prostate Tissues as Defined by Biopsy, MRI, and 3D MRSI." Magn Reson Med. Aug. 1989; 11 (2):209-20.

Narayan P, Vigneron DB, Jajodia P, Anderson CM, Hedgecock MW, Tanagho EA, James TL. "Tranrectal Probe got 1H MRI and 31P MR spectroscopy of the protstate gland." Urol Res. 1991;19(6):349-52.

Hering F, Muller S. "#1P MR spectroscopy and 1H MR Imaging of the human prostate using a transrectal probe." Magn Reson Med. Mar. 1988;6(3):353-64.

Martin JF, Hajek P., Baker L, Gylys-Morin V, Fitzmorris-Glass R, Mattrey RR. "Inflatable surface coil for MR imaging of the prostate." Radiology. Apr. 1998; 187(1):268-70.

Kurhanewicz J. Thomas A, Jajodia P, Weiner MW, James TL, Vigneron DB, Narayan P. "31P spectroscopy of the human prostate gland in vivo using a transrectal probe." Magn Reson Med. Dec. 1991;22(2):404-13.

Schnall MD, Lenkinski RE, Pollack HM, Imai Y, Kressel HY. "Prostate:MR imaging with an endorectal surface coil." Radiology. Aug. 1989; 172(2):570-4.

Desouza NM, Gilderdale DJ, Puni R, Coutts GA, Young IR. "A solid reusable endrectal receiver coil for magnetic resonance imaging of the prostate: design, use and comparison witha an inflatable endrectal coil." J Magn Reson Imaging. Sep.-Oct. 1996;6(5):801-4.

* cited by examiner

FIGURE 7

SYSTEMS, METHODS AND APPARATUS FOR AN ENDO-RECTAL RECEIVE-ONLY PROBE

ORIGIN

This invention was made with Government support by Grant Nos. CA59897, awarded by the National Institutes of Health. The Government has certain rights in this invention.

FIELD OF THE INVENTION

This invention relates generally to Magnetic Resonance Imaging and Magnetic Resonance Spectroscopy medical diagnostic devices, and more particularly to Magnetic Resonance Imaging and Magnetic Resonance Spectroscopy medical devices used to diagnose and assess pelvic pathologies, including prostate cancer.

BACKGROUND OF THE INVENTION

The value of Magnetic Resonance Imaging (MRI) devices for medical use was recognized almost immediately after they first appeared in the 1970s. Because they appear both to do no harm to the human body, and to create better images of the body's interior than the best X-ray technology, they have gained widespread use for diagnosis, pre-operative examination and even for assistance during surgical procedures. While MRI provides information on size and location of pathological abnormalities such as tumors, a variation of magnetic resonance technology called Magnetic Resonance Spectroscopy (MRS)—which identifies various biochemicals and their concentrations—often can help further by providing more information on the tissue chemistry of the target abnormality.

The typical MRI/MRS process consists first in the magnetic alignment of nuclei of a particular target nuclear species by a static main magnetic field produced by a solenoid magnet apparatus, arranged so that the cylindrical space bounded by the solenoid windings (i.e. the main magnet bore) forms a convenient space and platform for placement of an object containing the target nuclei. This application of the main magnetic field is followed by a sequence of pulses of a second magnetic field, by means of a RF (Radio Frequency) pulse generator, RF transmitter amplifier, and RF volume resonator (i.e. near-field transmit antenna). The result of this sequential pulsing is a perturbed magnetization of the target nuclei, transverse to the main field, in which condition the perturbed magnetization precesses about the main field. The Larmor frequency of the target nuclear species—the characteristic frequency of precession of target nuclei at a given strength of the main magnetic field—is linearly proportional to the strength of the main magnetic field. During precession, the magnetization is further perturbed by a sequence of magnetic gradient pulses, applied by means of pulse generators and gradient induction coils, which produce variations of the main magnetic field strength. At pre-selected intervals throughout the precession period, RF signals arising from the precessing target nuclei are detected at their characteristic frequencies by a tuned RF near-field receive antenna and the signals are fed through an RF receiver and image processing apparatus in order to compute and display images and/or spectra of the target nuclei.

The clinical use MRI/MRS technology is based on detecting and interpreting radio frequency RF excitation originating from target atomic nuclei in human tissue in response to manipulation of those nuclei with magnetic fields in a manner similar to that outlined above.

The distance from a large radio-frequency near-field antenna (or 'coil' as it is known in the art) to the tissue in question can be so great as to render said coil unable to provide the necessary strength of signal required for the level of detail and accuracy needed for proper evaluation of the target tissue. A greater distance means a weaker signal. Yet, the strength of the RF signal received from the nuclei is of fundamental importance both to the accuracy of the details of the image produced and the information on tissue chemistry.

Ongoing research and development of MRI/MRS technology has sought to use smaller 'local' coils, placed nearer the location of the tissue in question so as improve the strength and quality of information carried by the RF signals generated by the tissue. One focus of this effort with local coils has been the endo-rectal coils used to analyze pelvic pathologies including prostate cancer. And while gains have been made, research for over 15 years has left significant room for improvement in the use of endo-rectal devices.

One particular need is to take advantage of the opportunities offered by dual-testing of more than one species of target nuclei during a single examination. In particular, a dual-test of the tissue in question using both proton and carbon-13 nuclei could greatly improve results.

The most common magnetic nucleus targeted in clinical MRI/MRS is a proton, that is to say, an ordinary hydrogen nucleus, which is valuable by virtue of its high abundance and nearly universal distribution in biological tissue, as well for the high intrinsic RF signal obtained from its large magnetic moment during the test procedure.

An excellent choice for improving the MRI/MRS analysis of the chemistry of the tissue is found in the nuclei of an isotope of carbon, carbon-13, which can be used to trace a multitude of metabolic processes and transformations in normal and diseased states. Although of very limited natural abundance and possessing a weak magnetic moment, recent advances in the technology of hyperpolarization, can enhance the magnetization of carbon-13, and, to make it available in the test tissue, it can be introduced into an imaging subject by the use of an exogenous bolus of a metabolite compound enriched in carbon-13 and subjected to hyperpolarization. The resulting strong exogenous signal overwhelms the endogenous carbon background signal in the body, and permits the tracing of sequential metabolic transformations, in healthy or diseased tissue.

But present endo-rectal technology can not reliably make use of two such signals—proton and carbon-13—during the same test. One issue is the signal quality limitations resulting from the circuitry design of today's endo-rectal devices, which cannot adequately block the wrong RF signals while gathering the right ones. The design of the body of the apparatus is also a source of error. The endo-rectal design commonly used at present for MRI/MRS examination of pelvic tissue abnormalities such as prostate cancer has an inflatable, or balloon, body, which encloses a large volume of air. This creates a large discontinuity in static magnetic susceptibility at the interface between antenna body and tissue, resulting in degradation of image quality and spectral quality.

For the reasons stated above, and for other reasons stated below which will become apparent to those skilled in the art upon reading and understanding the present specification, there is a need in the art for improved reception of RF signals originating from tissue in response to magnetic fields generated by MRI/MRS technology. This means a continued need to place the antenna close to the prostate, while improving the general quality of RF signal reception from one or more species of target nuclei. Such an improvement would be especially valuable for the use of carbon-13 in MRI/MRS.

The above-mentioned shortcomings, disadvantages and problems are addressed herein, which will be understood by reading and studying the following specification.

SUMMARY

An endo-rectal receive-only probe is used as the component that receives radio frequency signals from human pelvic tissue, including prostate tissue, as part of a diagnostic system that includes magnetic resonance imaging and/or spectroscopy. In an economy of circuitry design and use of space appropriate to the insertable use of the apparatus, the compact, flattened pod of the endo-rectal probe contains the receive coils for the characteristic radio signals from each of two different magnetically re-oriented nuclear species as well as circuitry to block external transmissions while capturing the target radio signals. And, to obviate the need for electrical adjustment of the circuits at the exam site, each of the circuits is pre-tuned to the characteristic radio frequency of only a single nuclear species.

The endo-rectal receive-only probe includes the insertable pod and an attached handle pod to facilitate insertion and positioning and to carry cables with radio frequency signal data to an imaging device. The housing of the endo-rectal receive-only probe is made of a sturdy, benign material, such as solid delrin rendering the endo-rectal receive-only probe both re-usable and safe. The solid construction of the housing of the insertable pod portion of the endo-rectal receive-only probe is also an improvement over the currently used inflatable endo-rectal probe, which causes static magnetic susceptibility at the interface between antenna and tissue, perturbing the homogeneity of the main static magnetic field, and causing degradation of image quality and spectral quality.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into several sections. In the first section, a system level overview is described. In the second section, apparatus of embodiments and methods are described. Finally, in the third section, a conclusion of the detailed description is provided.

The object of a clinical MRS/MRI procedure is to enable an examination which combines a preliminary stage of proton imaging and spectroscopy together with other target nuclei that can improve the analysis of the chemistry of the tissue in question.

System Level Overview

An object of the invention is to make available an improved system for MRI/MRS examination of human pelvic abnormalities, including prostate cancer, using data from the radio signals of more than one species of nuclei in the prostate tissue. In one embodiment, two nuclei are used, protons and an isotope of carbon, carbon-13.

Figure 1:
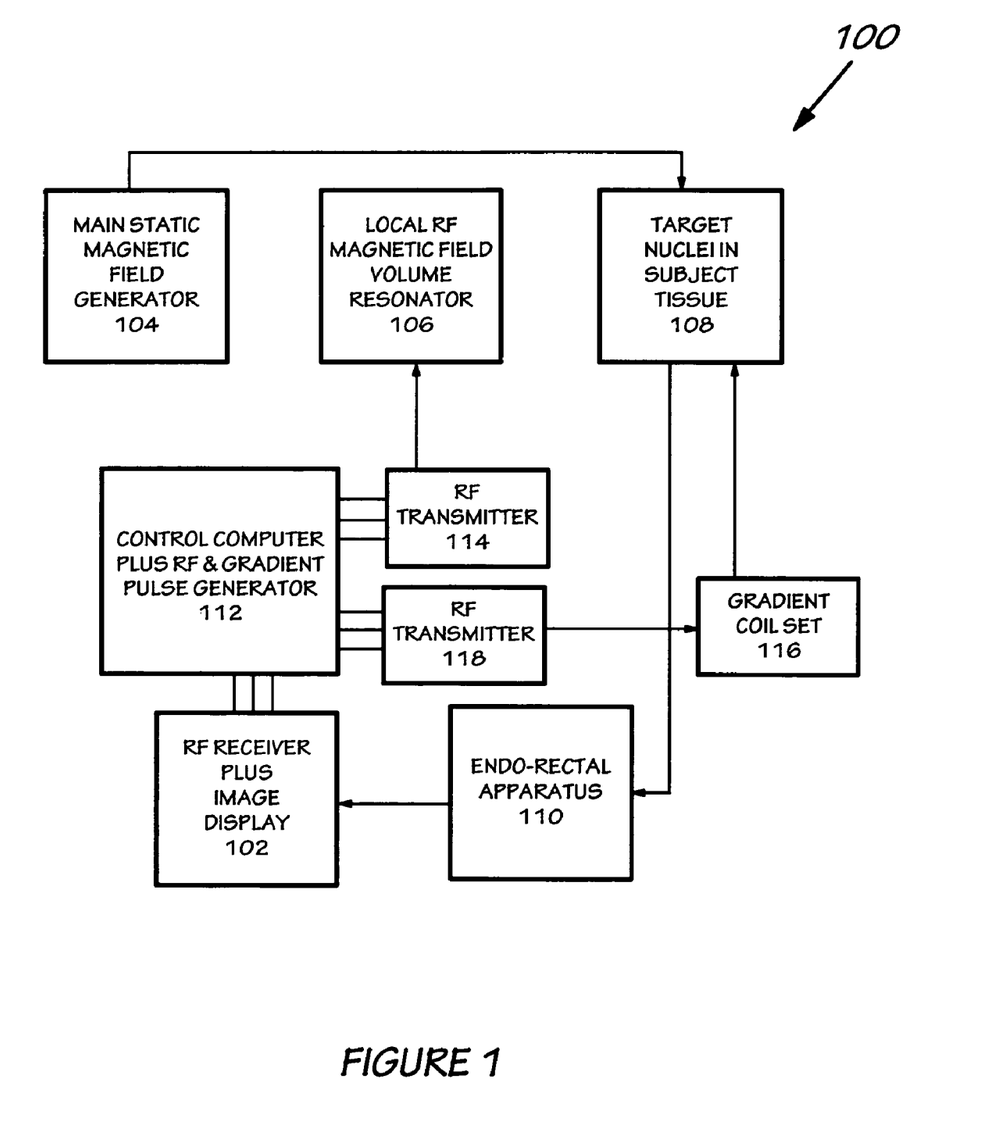
FIG. 1 is a block diagram of the components required for an MRI/MRS examination of the prostate, including magnetic field generators, target nuclei, endo-rectal apparatus, radio frequency circuitry, the control computer and gradient pulse generator, a gradient coil set, and a device for image display.

FIG. 1 is a block diagram of an overview of the MRI/MRS technology used for clinical evaluation of the prostate. System 100 is able to solve the need in the art for improved image quality and tissue information when using MRI/MRS for assessing prostate abnormalities. This improved image quality and tissue information is made possible by endo-rectal apparatus 110 which maximizes the clarity of RF signals generated by proton and carbon-13 nuclei during MRI/MRS scans.

Figure 2:
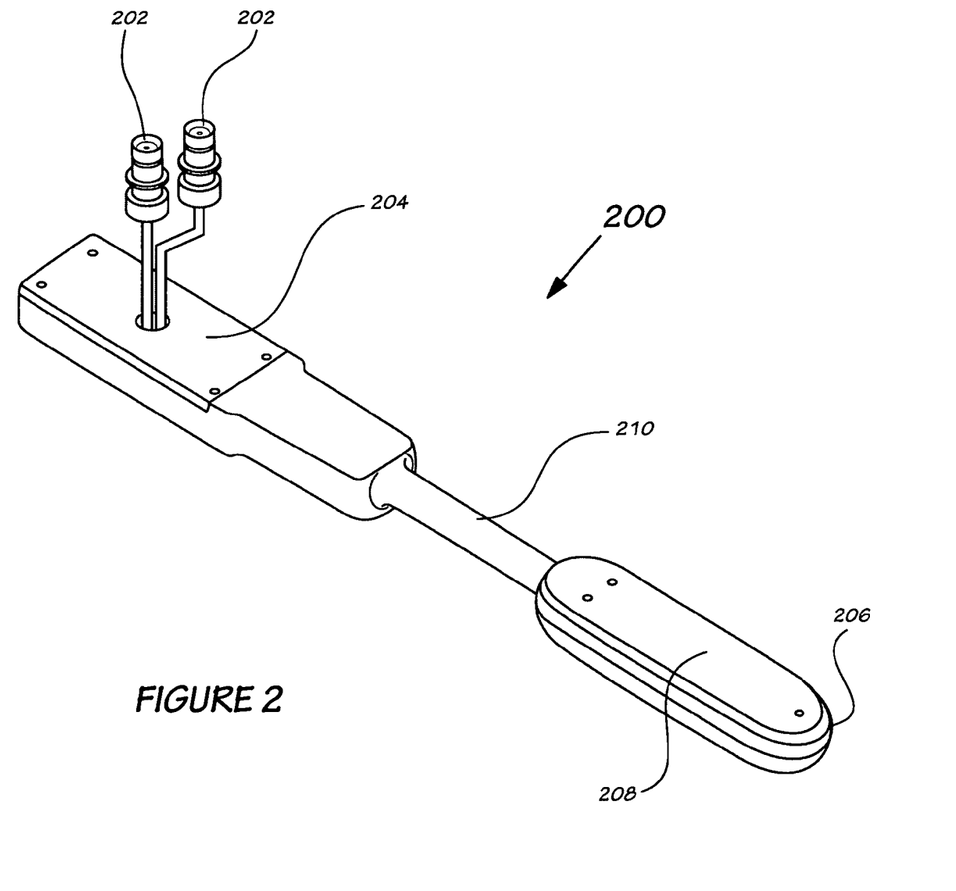
FIG. 2 is a view of the mechanical body of the apparatus seen fully assembled, with radio frequency cables protruding from the rectangular handle of the apparatus joined through a cylindrical RF cable channel to antenna circuitry enclosed in the pod which is to be inserted into the rectum in proper orientation and in close proximity to the target tissue.

FIG. 2 is a view of the mechanical body of the apparatus seen fully assembled, with radio frequency (RF) cables protruding from the handle of the device and antenna circuitry enclosed in the pod which is to be inserted into the rectum in close proximity to the target tissue. A handle 204 attached to insertable pod 106 is joined by cylindrical housing 210 that provides a channel for the RF cables 202 to connect to antenna circuitry 206.

An MRI/MRS exam using System 100 begins with the introduction of carbon-13 into the patient's prostate as part of target nuclei in subject tissue 108, positioning the patient, and inserting the endo-rectal apparatus 110. Then the main magnetic field generators 104 are applied, using the main field to disturb the magnetic orientation of the proton nuclei and using device 112 to generate RF pulses to the local volume resonator magnetic field 106 via RF transmitter 114, magnetic pulses to gradient coil set 116 using gradient transmitter 118 to perturb the magnetic orientation of proton and carbon-13 nuclei. This disturbance of the magnetic orientation of these carbon-13 and proton nuclei produces characteristic RF signals from the target carbon-13 and proton nuclei within the subject tissue. The antennas of the endo-rectal apparatus 110 receive these characteristic RF signals and send those same characteristic RF signals to the image display 102.

This compact endo-rectal apparatus 110 and the endo-rectal apparatus 110 circuitry are seen in FIGS. 2-6, and discussed below.

System 100 with the endo-rectal apparatus 110 discussed below is not limited to detecting or evaluating only a single pelvic pathology, including prostate cancer, nor to using data from only single-proton nuclei and carbon-13, as will be understood through the following discussion.

Apparatus Embodiments

In the previous section, a system level overview of the operation of an embodiment of the invention was described. The endo-rectal apparatus 110 solves the need in the art to superimpose two receive antenna loop and associated circuitry in close proximity to the prostate, while improving the quality of the RF signal information when both carbon-13 and proton nuclei as target nuclei for the MRI/MRS examination. By having circuitry tuned only to the RF signals of the desired target nuclei, the apparatus also solves the need in the art to tuning of the receive antennas on site during the exam. The mechanical body of the apparatus is strong, durable and safe to use.

In this section, the particular apparatus of such an embodiment is described by reference to a series of diagrams. Such an embodiment is the endo-rectal apparatus 110 of the MRI/MRS system shown in FIG. 1.

Figure 3:
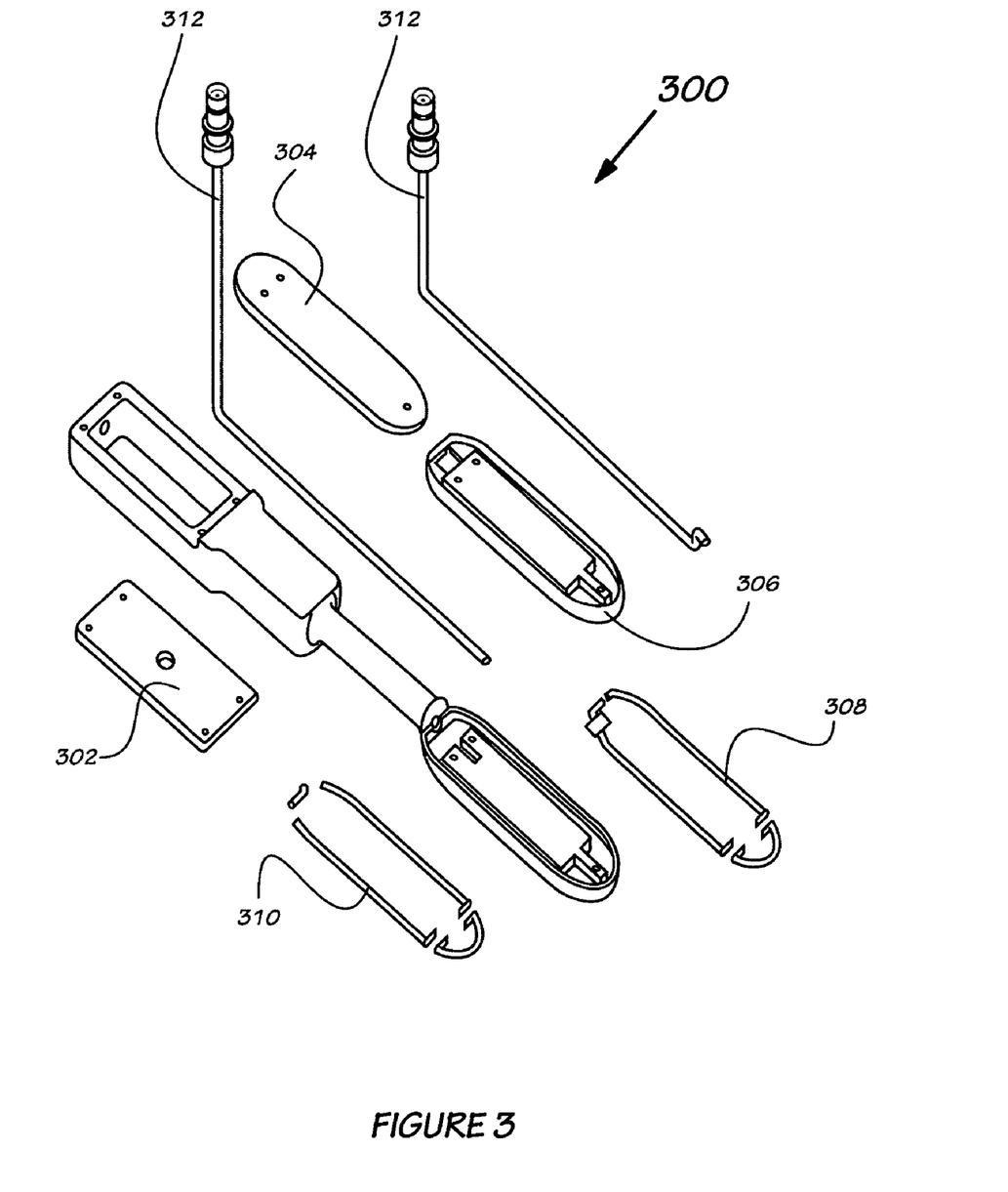
FIG. 3 is an exploded view of the apparatus showing the top covers of both the handle and the pod assembly, and including the platform for the carbon circuit and circuit components.
Figure 4:
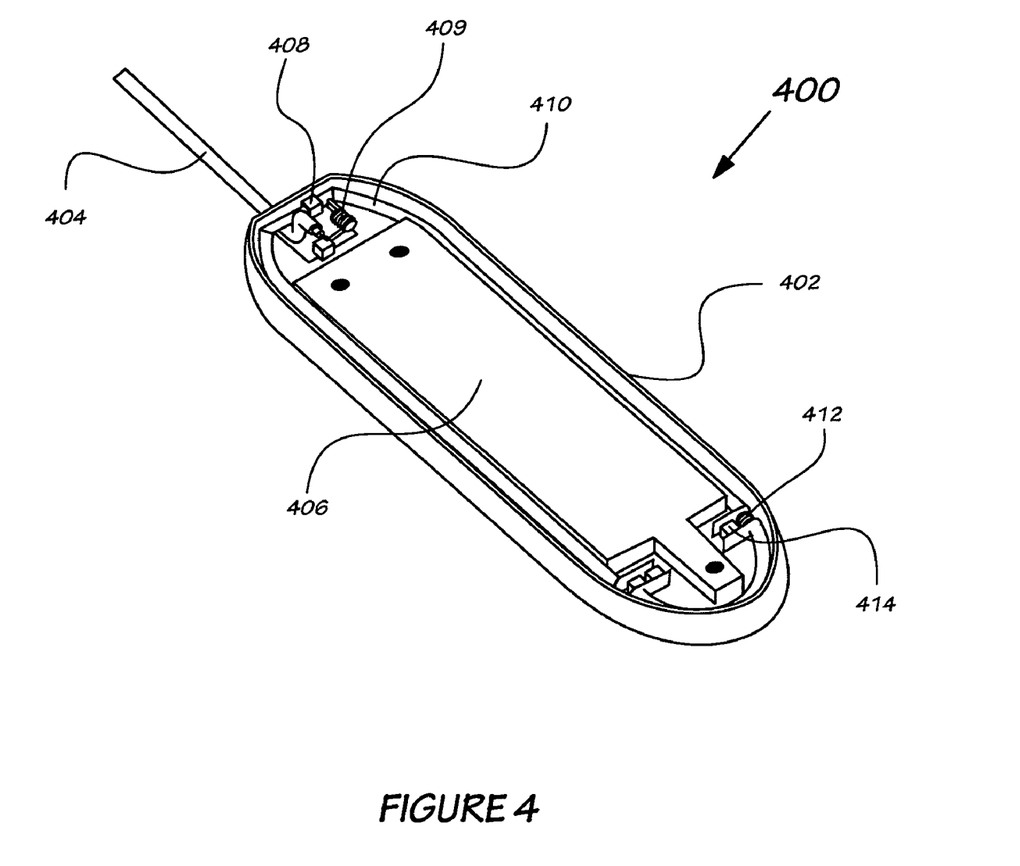
FIG. 4 is a close-up view of the proton circuitry assembly.
Figure 5:
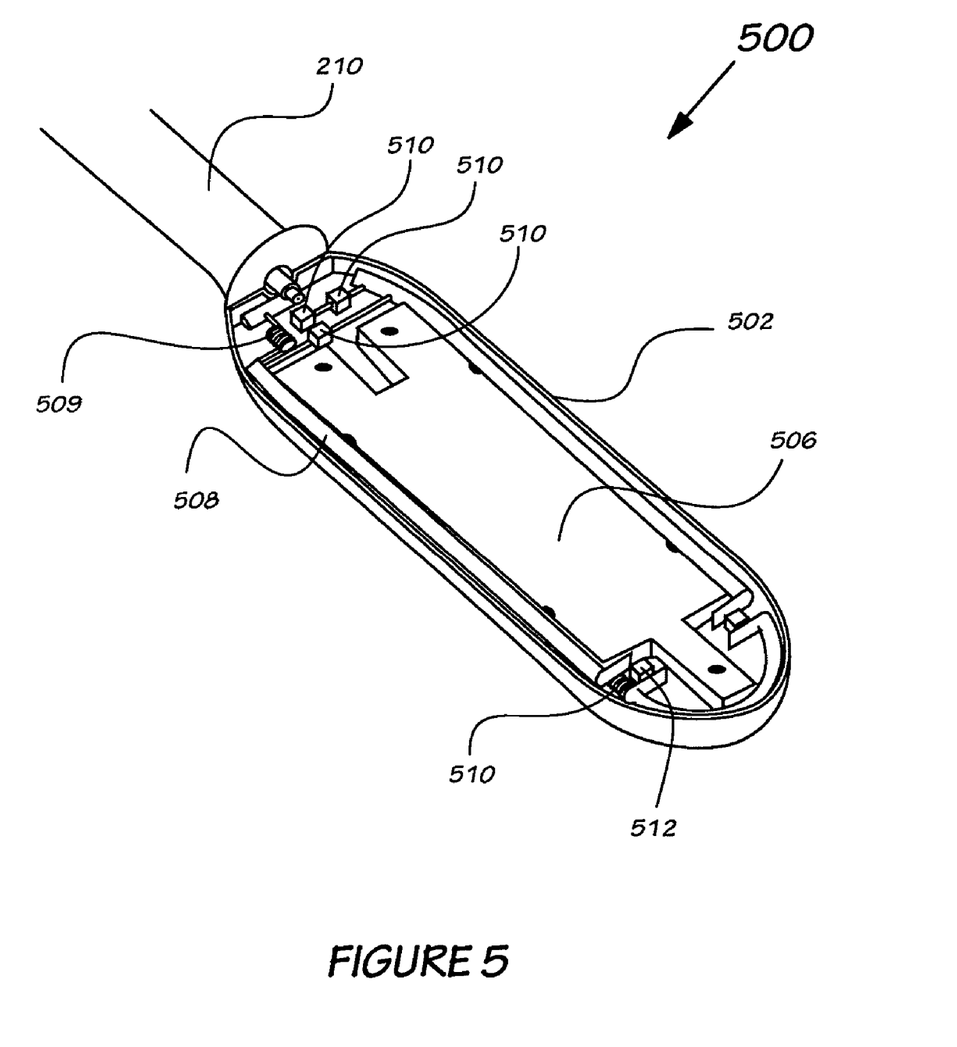
FIG. 5 is a close-up view of the carbon circuit subassembly which fits atop the proton circuitry.

FIGS. 2-5 offers views of the endo-rectal apparatus 110 and various components of the endo-rectal apparatus 110. FIG. 2 is a view of the mechanical body of the endo-rectal apparatus 110 of FIG. 1 seen fully assembled, with Radio Frequency (RF) cables 202 protruding from the handle 204 of the apparatus joined through channel 210 to antenna circuitry 206 enclosed in the pod 208 which is to be inserted into the rectum in proper orientation and in close proximity to the target tissue. FIG. 3 is an exploded view of the apparatus showing the top cover 302 of the handle 204 and the top cover 304 of the pod 208, and including the platform 306 for the carbon circuit, resonant loop 308 for detecting target carbon nuclei RF signals and resonant loop 310 for detecting proton nuclei RF signals. FIG. 4 is a close-up view of the carbon circuit subassembly 402 which fits atop the proton circuit assembly of the pod 208, showing loop coil 410, circuit components 408, 409, 412, and 414, cover 404 of RF cables, and the subassembly platform 406 is covered by said top cover 304 of the pod 208. FIG. 5 is a close-up view of the proton circuit assembly 502 in pod 208, showing loop coil 508, circuit components 509, 510, and 512, RF cable housing channel 210, and assembly platform 506, over which is fitted the carbon circuit subassembly 402.

The mechanical body of the apparatus, shown in FIGS. 2-5, is a sturdy, compact, reusable housing. In this embodiment, the housing of the apparatus is made of solid delrin, which provides strength and durability while minimizing any possibility of abrasion or of tissue damage from the chemistry of pod 208. The shallow curvature of the top of the pod cover 304 allows for close placement to the prostate of the circuitry's resonant loops, maximizing RF reception from target nuclei while minimizing discomfort or injury during the positioning of the pod for optimal RF reception from target nuclei.

The RF signals of interest in this embodiment are from protons (hydrogen nuclei) and an isotope of carbon, carbon-13. While hydrogen is plentiful in the water found in human tissue, carbon-13 is not likely to be found at all. For this reason, and because, unlike carbon-12, a hyperpolarized carbon-13 nucleus can have a magnetic moment that will react to the pulses of a magnetic field by generating RF signals whose source can only be the prostate, introducing it into the prostate can greatly enhance the data obtained by the procedure.

Figure 6:
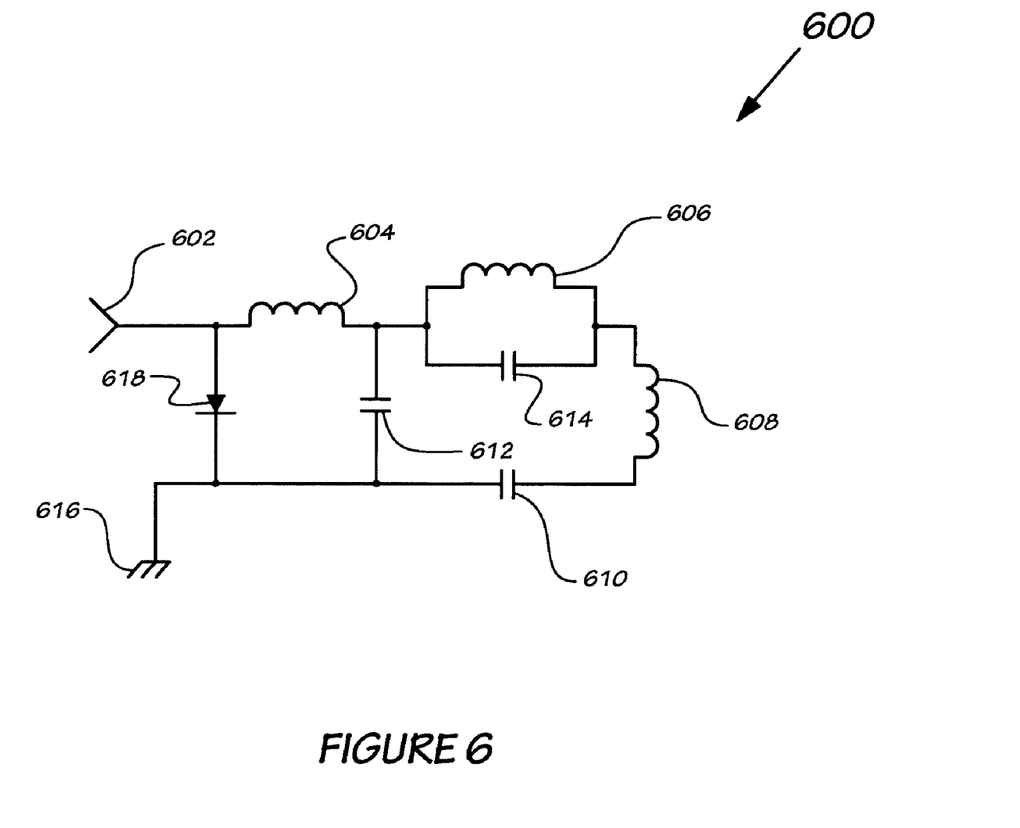
FIG. 6 is a schematic of the carbon circuit, showing the arrangement of the carbon circuit component inductors, capacitors and diode.
Figure 7:
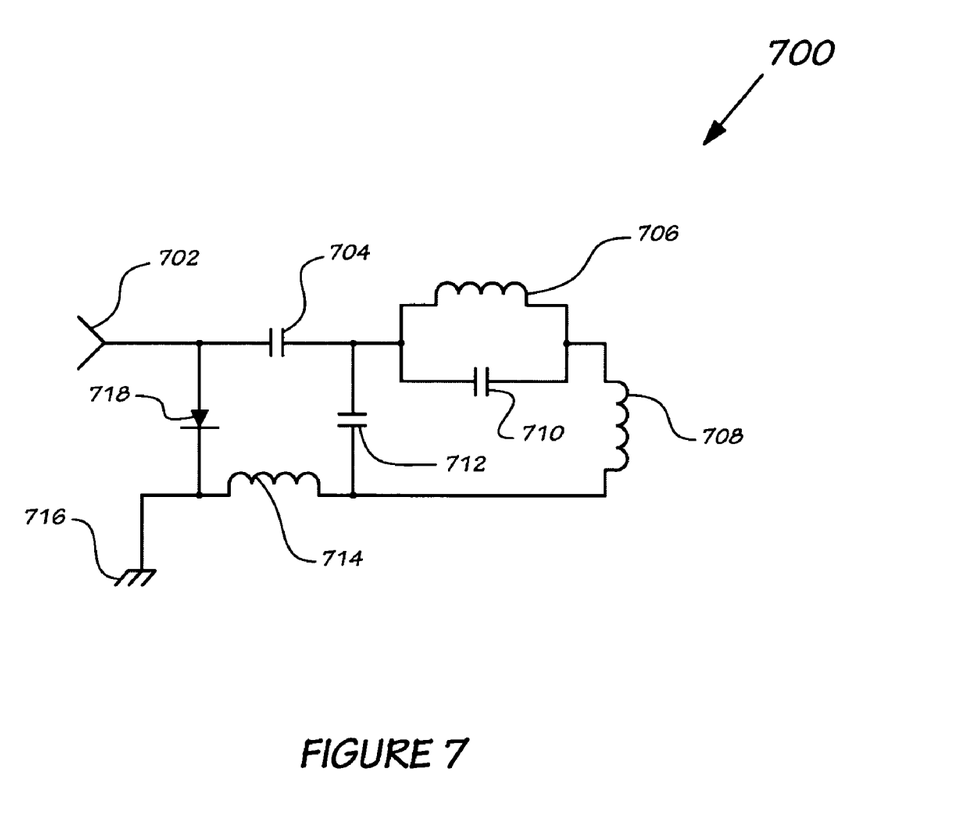
FIG. 7 is a schematic of the proton circuit, showing the arrangement of its component inductors, capacitors and diode.

FIGS. 6 and 7 are schematics of the carbon and proton circuits that solve the need in the art for RF reception circuitry that minimizes RF signal interference during MRI/MRS data gathering. And the carbon and proton circuits do so in an unusual economy of space, where all circuit components are located within the pod 208. As a result, the apparatus also solves the need in the art to obviate external circuitry during the procedure. The novel circuit layout minimizes extraneous losses by placing all matching and decoupling components proximal to the actual receiver coils so that sections of unmatched transmission line are avoided entirely. The apparatus has a RF receiver coil 308 for the carbon circuit and a separate RF receiver coil 310 for the proton circuit on which the platform for the carbon circuit is superimposed within pod 208. Each receiver coil has an active pin diode circuit for blocking an external transmitter at an operating frequency of the receiver coil, as well as a passive block at the operating frequency of its neighboring coil.

FIG. 6 is a schematic of the carbon circuit, showing the arrangement of component inductors, capacitors and diode of the carbon circuit. FIG. 7 is a schematic of the proton circuit, similarly showing its arrangement of circuit elements. Both circuits are discussed in detail below.

The design of the circuits seen in figures make possible the efficient reception of data from both carbon-13 and proton nuclei from within the endo-rectal probe.

The most efficient antennae for MRI is a loop of conductive material which can carry an electric current. But when a dual antenna is fabricated of two loops, each loop tuned respectively to an operating frequency of the loop with loops constrained to lie parallel to each other and superimposed in close proximity, the loops will cross couple, and exchange energy, and the signal in one loop—rather than remain pure—ordinarily will be contaminated with interfering signals arising from the neighbor loop.

However, this interference problem of parallel loops is avoided in this embodiment by the introduction into each loop of a passive parallel tuned LC circuit, or trap, as it is known in the circuit art. For a proton-carbon dual antenna, the proton receive loop is fitted with a trap tuned to carbon Larmor frequency, and the carbon receive loop is fitted, vice versa, with a trap tuned to proton Larmor frequency. The trap circuit is physically small in comparison to the actual reception loop at a given frequency. While it is known in the circuit and antenna arts that coupling between two loops may be reduced by disposing them in mutually orthogonal (as opposed to parallel) geometry, the goal of optimal reception of MR (Magnetic Resonance) signals from the human prostate demands a parallel geometry in which the windings of both loops are as close as may be to the prostate tissue. The traps are passive in nature, as opposed to switch-activated, and are therefore unchanging in their functional, electrical behavior, throughout the cycles of transmission and reception, which comprise the course of the MRI/MRS examination.

Alternation of cycles of transmission and reception poses another problem for the dual receive antenna. Since a single loop antenna produces an RF magnetic field which is spatially inhomogeneous, it is desirable, for transmission purposes, to have a larger transmitter, consisting of multiple loops, such as a Helmholtz pair, or a birdcage resonator, which produces a spatially homogeneous field. However, such a larger transmitter coil will deposit significant RF energy into a tuned but unprotected receiver antenna, causing, in a clinical medical examination, possible injury to the patient, not to mention damage to the receive antenna. Consequently, in addition to the passive traps for circuit decoupling, the dual receive antenna is fitted with a pair of active traps to detune the resonant receive loops during the transmit cycle only, and prevent thereby the harmful deposition of radio frequency energy during the transmit cycle. These active traps for transmitter blocking function only during the transmit cycle, and are (by means of an activated pin diode circuit) switched on during the transmit cycle, and off the during the receive cycle.

The switching of these active traps is in contradistinction to the passive traps, which are not switched. Furthermore, the active traps for transmitter blocking are each tuned to the Larmor frequency of the respective receive loop of the active trap, i.e. the carbon loop has its transmit-blocking trap tuned to carbon frequency, and its circuit de-coupling trap tuned for proton frequency, while the proton circuit has its transmit-blocking trap tuned to proton frequency and its circuit de-coupling trap tuned for carbon frequency.

An advantage of the dual-receive antenna of the endo-rectal apparatus is that the dual-receive antenna has a totality of four traps—two active and two passive—and is therefore dual-tuned in the channels of the dual-receive antenna, and each channel is dual-blocked.

The active block presents certain unique problems in a loop antenna small enough for an endo-rectal probe. The active block, as illustrated for the carbon circuit in FIG. 6, uses the shunt impedance matching capacitor 612 (whose value is predetermined by the necessity of presenting a load to input coupling port 602 in concert with series inductor 604, which is chosen to resonate at the carbon Larmor frequency with said matching capacitor. When pin-diode 618 is energized, capacitor 612 and inductor 604 form a parallel resonant combination, presenting a high impedance, which will tend to stop, or significantly inhibit the circulation of any current through reception coil 608. Since receive loop 608 is the site at which, if unprotected, a harmful excess of transmitter power would be deposited, stopping such current flow is necessary to protect both patient and antenna.

Further, the impedance of the blocking circuit rises with the value of the blocking inductance (604), and yet the designer is not at liberty to maximize said inductance, but must choose a value resonant with aforesaid matching capacitor. While this presents no problems for the carbon-13 Larmor frequency, the situation is different at the proton Larmor frequency. Given the value required for a shunt match capacitor, the requisite value of blocking inductor would be too small for adequate blocking.

The solution to this problem is illustrated in FIG. 7. A matching network may comprise a series instead of a shunt capacitor, and the value of the series capacitor is typically much smaller than the shunt. Therefore, in the circuit of FIG. 7, shunt capacitor 712 is not, by itself, the match capacitor, but functions in tandem with series capacitor 704, which is much smaller in value than 712; and the net series effective capacitance is smaller still. This means that blocking inductor 714 may be increased in value several fold over the value it would have in a circuit with pure shunt matching; and the net result of this increased inductance is higher impedance and therefore improved performance in the blocking circuit when pin diode 718 is energized. The impedance presented to the receive loop (inductor 708) is topologically equivalent to that in the blocking circuit of FIG. 6. The circuit is now characterized by what can be called an 'inductive imbalance'—a virtual ground that ordinarily would exist in the middle of inductor 708, but is now displaced, due to the presence of inductor 714. But rather than constitute an extra loss mechanism, the impedances in question are small enough to negate the importance of any loss mechanism. The use of inductive imbalance in a series match circuit is a key to improving blocking in the circuitry of the endo-rectal apparatus, and an advantage of the apparatus.

With reference to FIG. 3, Radio Frequency signals are coupled out of the antenna via the pair of semi-rigid transmission lines 312, which are depicted as having right angle bends over the handle (enclosed by cover 302), which is otherwise empty. The insertable pod (enclosed by cover 304) contains all discrete circuit elements described hereinabove, including the reception loops 308 and 310. Greater detail is given in FIG. 4 (detail of carbon circuit) and FIG. 5 (detail of proton circuit). Shunt capacitor 408 and inductor 409, corresponding to elements 612 and 604 (active trap) in schematic FIG. 6. Similarly elements 412 and 414 comprise the passive trap shown in 606 and 614. Similarly, in FIG. 5, blocking inductor 509 corresponds to inductor 714, and grouped elements 510 correspond collectively to capacitors 704 and 712, and to diode (cathode rectifier) 718. The passive trap in FIG. 7 is inductor 706 and capacitor 710. It is therefore seen that all discrete circuit elements touching the dual tuning and dual double blocking are contained within the insertable pod, and none of these is relegated to the handle at the other end of the apparatus. This compact grouping of circuit elements allows for efficient action of the active traps, and also increases the overall efficiency of the reception circuits by placing impedance matching directly at the juncture of circuit and transmission line, rather than running sections of unmatched line through pod-connecting channel 210. As such, the compact grouping of all trapping and impedance matching circuitry, and the avoidance of unmatched sections of transmission line are significant advantages of the apparatus.

The circuitry of the apparatus demonstrates good impedance matching at both carbon and proton signal frequencies, and good isolation between channels despite the parallelism and proximity of the coils located within the insertable pod 208.

Yet another advantage of the apparatus is that proton and carbon circuits of the apparatus solve a need in the art obviate tuning of the circuits at the examination site for the characteristic frequencies of the target nuclei. In order to be useful for diagnosis and prognosis, the RF signals generated by certain nuclei in the target tissue must be received with minimal signal interference. The target nuclei for the MRI/MRS scan of the tissue in question are protons—hydrogen nuclei—and the carbon atoms of hydrocarbons. Each of these nuclei generate their own characteristic RF signals. In order to maximize the clarity of the signals generated by these nuclei, the endo-rectal's apparatus's circuitry for carbon, shown in FIG. 6, is permanently tuned to the RF signal generated by carbon, while the proton circuitry, shown in FIG. 5, is permanently tuned to the RF signal generated by the proton nuclei of hydrogen. This eliminates the need to tune the circuitry during an examination, improving clinical efficiency and accuracy. In the case of an AM radio, which must be capable of receiving a variety of different frequencies, the tuning knob permits the listener to alter the values of the capacitor in the receiver circuit so as to pick up one frequency rather than another. Unlike said radio receivers, the circuitry of the subject endo-rectal apparatus is preset to receive only the RF signals of the frequencies of target nuclei.

In another embodiment the circuitry of the apparatus is permanently tuned to receive RF signals from hydrogen nuclei (protons) and from phosphorous nuclei, rather than carbon nuclei. Tunings for other nuclei are, of course, possible and within the scope of the invention.

CONCLUSION

An endo-rectal receive-only apparatus for use in MRI/MRS scanning for clinical diagnosis and prognosis of the prostate is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. For example, although described in terms used in medical science and in radio technology, one of ordinary skill in the art will appreciate that implementations can be made for other uses, including petroleum studies and materials science, where the technology provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future medical devices, different atomic nuclei, and new scientific technologies.

The terminology used in this application with respect to systems and apparatus is meant to include all MRI/MRS environments and alternate technologies which provide the same functionality as described herein.

We claim:

1. An apparatus to receive radio frequency signals characteristic of a targeted specimen within a patient, the apparatus comprising:
   a housing designed to be inserted into a patient; and
   at least two radio frequency receiver coils, each of which (i) is positioned inside the housing, (ii) has an operating radio frequency, and (iii) includes:
      a first circuit proximal to the radio frequency receiver coil operable to block an external transmitter only during a transmit cycle at an operating radio frequency of the circuit and
      a second circuit operable to provide a passive block at the operating radio frequency of other ones of the radio frequency coils;
   wherein each circuit is operable to seek only a single frequency,
   wherein the radio frequency receiver coils are superimposed upon each other,
   wherein the first circuit and the second circuit respectively associated with each of the at least two radio frequency receiver coils provide at least two active traps and two passive traps,
   wherein the radio frequency signals received by the at least two receiver coils are generated by different target nuclei associated with the specimen.

2. The apparatus of claim 1, wherein the circuit of each radio frequency receiver coil receives radio frequency signals from human tissue.

3. The apparatus of claim 2, wherein the circuit of each radio frequency receiver coil sends radio frequency signals to an imaging device.

4. The apparatus of claim 3 wherein the circuit of one radio frequency receiver coil is pre-tuned to receive only radio frequency signals characteristic of magnetically disturbed carbon-13 nuclei.

5. The apparatus of claim 3 wherein the circuit of one radio frequency receiver coil is pre-tuned to receive only radio frequency signals characteristic of magnetically disturbed hydrogen nuclei.

6. The apparatus of claim 3 wherein the circuit of each radio frequency receiver coil sends radio frequency signals to an imaging device that is part of an MRI/MRS medical diagnostic system.

7. The apparatus of claim 3, wherein the circuit of one radio frequency receiver coil is pre-tuned to receive only radio frequency signals characteristic of proton Larmor frequency.

8. The apparatus of claim 3, wherein the circuit of one radio frequency receiver coil is pre-tuned to receive only radio frequency signals characteristic of proton Larmor frequency.

9. The apparatus of claim 2, wherein the circuit of each radio frequency receiver coil receives radio frequency signals from human tissue that is prostate tissue.

10. The apparatus of claim 1, wherein the circuit of at least one radio frequency
   receiver coil receives radio frequency signals from human tissue containing carbon-13.

11. The apparatus of claim 1 wherein the apparatus further comprises a circuit that is pre-tuned to receive only the radio frequency characteristic of magnetically disturbed phosphorous nuclei.

12. The apparatus of claim 1 wherein the insertable housing further comprises:
   a re-usable portion.

13. The apparatus of claim 1 wherein the apparatus further comprises:
   a pod and a handle containing the circuits and associated coils of the apparatus, said pod separate from the handle of the apparatus and insertable into a patient.

14. The apparatus of claim 13 wherein the pod further comprises:
   a top cover no higher than needed to cover the internal circuitry and coils.

15. The apparatus of claim 1, wherein the apparatus is a component of a system which uses magnetic resonance imaging/magnetic resonance spectroscopy to generate radio frequency signals.

16. The apparatus of claim 15 wherein the apparatus is a component of a system which uses magnetic resonance imaging/magnetic resonance spectroscopy to generate radio frequency signals in human tissue for clinical diagnosis.

17. A method of receiving radio frequency signals characteristic of a targeted specimen using the apparatus of claim 1 wherein said first blocking circuits are activated by an external switching apparatus.

18. A method of receiving radio frequency signals characteristic of a targeted specimen using the apparatus of claim 1 wherein radio signals from carbon-13 nuclei received by the circuit of a radio frequency receiver coil of claim 1 are generated from carbon-13 nuclei magnetically disturbed by a volume field generator.

19. A method of receiving radio frequency signals characteristic of a targeted specimen using the apparatus of claim 1 wherein radio signals from hydrogen nuclei received by the circuit of a radio frequency receiver coil of claim 1 are generated from hydrogen nuclei magnetically disturbed by the main magnetic field generated by an MRI/MRS medical diagnostic system.

20. The apparatus of claim 1, wherein the circuit of one radio frequency receiver coil is pre-tuned to receive only radio frequency signals characteristic of a carbon Larmor frequency.

21. The apparatus of claim 1, wherein the circuit of one radio frequency receiver coil is pre-tuned to receive only radio frequency signals characteristic of a carbon-13 Larmor frequency.

* * * * *

UNITED STATES PATENT AND TRADEMARK OFFICE
CERTIFICATE OF CORRECTION

PATENT NO. : 7,945,308 B2
APPLICATION NO. : 11/320361
DATED : May 17, 2011
INVENTOR(S) : James S. Tropp et al.

It is certified that error appears in the above-identified patent and that said Letters Patent is hereby corrected as shown below:

On the Title Page, Item (74), "Attorney, Agent of Firm" should be corrected to delete "Jean Tibbetts, Esq."

Signed and Sealed this
Second Day of October, 2012

David J. Kappos
*Director of the United States Patent and Trademark Office*